United States Patent [19]

Kugele

[11] 4,118,371

[45] Oct. 3, 1978

[54] ORGANOTIN MERCAPTOALKANOL ESTER SULFIDE STABILIZERS FOR PVC RESINS

[75] Inventor: Thomas Gordon Kugele, Cincinnati, Ohio

[73] Assignee: Cincinnati Milacron Chemicals Inc., Reading, Ohio

[21] Appl. No.: 792,257

[22] Filed: Apr. 29, 1977

[51] Int. Cl.$^2$ .................. C08K 5/58; C07F 7/22
[52] U.S. Cl. .................. 260/45.75 S; 260/45.75 T; 260/429.7
[58] Field of Search .................. 260/45.75 T, 45.75 S, 260/429.7

[56] References Cited

U.S. PATENT DOCUMENTS

| | | | |
|---|---|---|---|
| 3,108,126 | 10/1963 | Crauland | 260/45.75 S |
| 3,413,264 | 11/1968 | Hechenbleikner et al. | 260/45.75 |
| 3,476,704 | 11/1969 | Shroeder et al. | 260/45.75 S |
| 3,565,931 | 2/1971 | Brecker | 260/45.75 S |
| 3,609,120 | 9/1971 | Hoye et al. | 260/45.75 S |
| 3,817,915 | 6/1974 | Kauder et al. | 260/45.75 K |
| 3,869,487 | 3/1975 | Kugele et al. | 260/45.75 S |
| 3,962,296 | 6/1976 | Chiba et al. | 260/429.7 |
| 3,970,678 | 7/1977 | Molt | 260/429.7 |

*Primary Examiner*—V. P. Hoke
*Attorney, Agent, or Firm*—Donald Dunn

[57] ABSTRACT

Halogen containing polymers are stabilized against deterioration by novel organotin mercaptoalkanol ester sulfides or polysulfides characterized by having at least one sulfide or polysulfide bridged tin to tin group and at least one oxygen containing organic group bonded to tin through a carbon atom.

43 Claims, No Drawings

ORGANOTIN MERCAPTOALKANOL ESTER SULFIDE STABILIZERS FOR PVC RESINS

FIELD OF INVENTION

This invention relates to novel organotin sulfide and polysulfide compounds, to polymer compositions containing the novel organotin sulfide and polysulfide compounds and to methods for stabilizing polymers by admixing therewith the novel organotin sulfide and polysulfide compounds.

BACKGROUND OF THE INVENTION

Organotin compounds, particularly useful for stabilizing halogen containing polymers, have been known in the art for quite some time. More recently organotin compounds having tin-sulfur bonds have been disclosed, particularly as stabilizers for PVC. Kauder et al, in U.S. Pat. No. 3,817,915, have taught organotin mercaptocarboxylic acid ester sulfides having both a hydrocarbon radical of from one to eighteen carbon atoms and a mercaptocarboxylic acid ester group bonded to the same tin atom. Kugele et al, U.S. Pat. No. 3,869,487 have taught organotin mercaptocarboxylic acid ester polysulfides having an alkyl group of one to eight carbon atoms or benzyl and a mercaptocarboxylic acid ester group bonded to the same tin atom. In both the Kauder et al and Kugele et al teachings the mercaptocarboxylic acid ester is bonded to the tin atom through the sulfur atom of the mercaptocarboxylic acid moiety. Organotin compounds having a monovalent alkyl group of one to eight carbon atoms and a mercaptoalkanol or derivative thereof bonded to the same tin atom, the mercaptoalkanol or derivative thereof being bonded to the tin through the sulfur atom of the mercaptoalkanol moiety, have been disclosed by Kugele et al in U.S. Pat. No. 3,979,359.

SUMMARY OF THE INVENTION

According to this invention there are provided novel organotin mercaptoalkanol ester sulfides and polysulfides.

DESCRIPTION OF THE INVENTION

In accordance with this invention there are provided (1) novel organotin mercaptoalkanol ester sulfides and polysulfides having at least one sulfide or polysulfide bridged tin to tin group, at least one mercaptoalkanol ester group bonded to a sulfide or polysulfide bridged tin atom through the sulfur atom of the mercaptoalkanol moiety and at least one oxygen containing organic group bonded to a sulfide or polysulfide bridged tin through a carbon atom, and having a carbon oxygen bond, (2) novel polymer compositions comprising an organic polymer and an organotin mercaptoalkanol ester sulfide or polysulfide having at least one sulfide or polysulfide bridged tin to tin group, at least one mercaptoalkanol ester group bonded to a sulfide or polysulfide bridged tin atom through the sulfur atom of the mercaptoalkanol moiety and at least one oxygen containing organic group having a carbon oxygen bond and bonded to a sulfide or polysulfide bridged tin atom through carbon, and (3) processes for stabilizing organic polymers comprising the step of mixing into the polymer the novel organotin mercaptoalkanol ester sulfide or polysulfide as previously described herein. The organotin mercaptoalkanol ester sulfides and polysulfides of this invention may be described in accordance with the following formulae

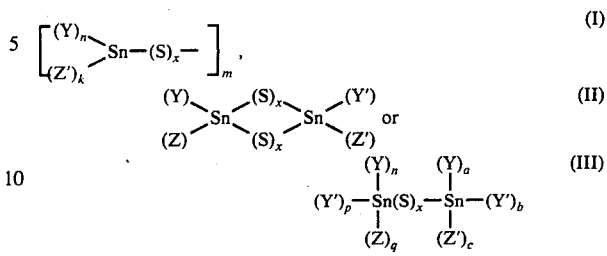

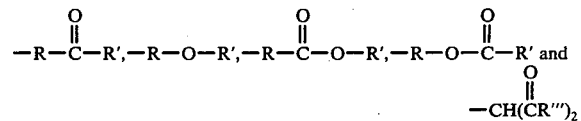

where
$a$ is 0 to 2, $b$ is 0 to 2, $c$ is 1 or 2, $a + b + c$ is 3,
$k$ is 1 or 2
$m$ is 3 to 10, $n$ is 1 or 2, $p$ is 0 or 1, $q$ is 1 or 2
$n + p + q$ is 3, $x$ is 1 to 4 and $n + k$ is 2 or 3,
Y is a member selected from the group consisting of

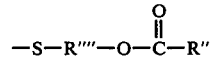

Z is

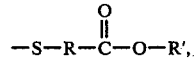

Y' is Y, $$-S-R-\overset{O}{\underset{\|}{C}}-O-R',$$

halogen of atomic weight 35 to 127 or alkyl of one to eighteen carbon atoms
Z' is Z or Y'
R is a bivalent hydrocarbon radical having one to four carbon atoms
R' is hydrogen or a monovalent hydrocarbon radical having one to twenty carbon atoms
R'' is alkyl of one to twenty carbon atoms branched or unbranched, saturated or olefinically unsaturated
R''' is alkyl of one to twenty carbon atoms or alkoxy of one to twenty carbon atoms
R'''' is a bivalent hydrocarbon radical having two to four carbon atoms
with the proviso that in formula I at least one Z' is

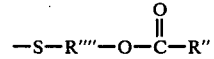

and the tin is tetravalent. In the practice of this invention R' may be hydrogen or monovalent hydrocarbon radical of one to twenty, preferably one to twelve more preferably one to five carbon atoms, and may be olefinically unsaturated, R'' may be alkyl of one to twenty, preferably eight to twenty carbon atoms, and may contain one or more olefinic double bonds, R''' may be alkyl of one to twenty, preferably one to twelve more preferably one to five carbon atoms or alkoxy of one to twenty, preferably one to twelve still more preferably one to five carbon atoms. With reference to formula (I) above m is preferably 3 to 6.

Polymer compositions in accordance with this invention more particularly are polymer compositions comprising an organic polymer, more especially a halogen containing organic polymer and an organotin mercaptoalkanol ester sulfide or polysulfide according to formula (I), (II) or (III) above.

The organotin mercaptoalkanol ester sulfides and polysulfides of this invention, more particularly the compounds of this invention according to formulae (I), (II) and (III) above, are useful as stabilizers, alone or in combination with known stabilizers, for stabilizing polymers, particularly halogen containing polymers more particularly vinyl chloride homopolymers and copolymers. The organotin mercaptoalkanol ester sulfides and polysulfides according to this invention find particular utility as heat stabilizers for vinyl chloride homopolymers and copolymers.

In accordance with this invention there are provided (1) novel organotin mercaptoalkanol ester sulfides and polysulfides, and (2) polymer, particularly halogenated polymer, compositions which contain organotin mercaptoalkanol ester sulfides and polysulfides having formula $$\left[ \begin{matrix} (Y)_n \\ (Z')_k \end{matrix} Sn-(S)_x- \right]_m \quad (I)$$

where the tin is tetravalent, $n$ is 1 or 2; $k$ is 1 or 2; $x$ is 1 to 4; $m$ is 3 to 10; Y is a member selected from the group consisting of $$-R-\overset{O}{\underset{\|}{C}}-R'; -R-O-R', -R-\overset{O}{\underset{\|}{C}}-O-R', -R-O-\overset{O}{\underset{\|}{C}}-R' \text{ and}$$

-continued
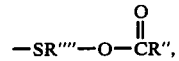

Y, alkyl of 1 to 18 carbon atoms or halogen of atomic weight 35 to 127, with the proviso that at least one Z' must be $$-SR''''-O-\overset{O}{\underset{\|}{C}}R'',$$

and where R is a $C_1$ to $C_4$ bivalent hydrocarbon radical, R' is hydrogen or $C_1$ to $C_{20}$ monovalent hydrocarbon radical, R'' is $C_1$ to $C_{20}$ saturated or olefinic unsaturated, branched or straight chain alkyl group, R''' is $C_1$ to $C_{20}$ saturated or olefinic unsaturated, branched or straight chain alkyl group or $C_1$ to $C_{20}$ straight or branched alkoxy group, R'''' is a bivalent $C_2$ to $C_4$ hydrocarbon radical. The compounds according to formula (I) may have a polymeric straight chain, a polymeric branched chain or a cyclic structure. As an example, a cyclic structure compound according to formula (I) may be described in accordance with theory as

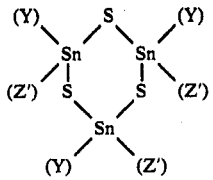

It is not intended that this invention according to formula (I) shall include compounds having obviously unstable, strained cyclic structures. Examples of compounds in accordance with formula (I) and of halogenated polymer, particularly vinyl halide homopolymer and copolymer, compositions containing same include but are not limited to, where

| n | k | x | m | Y | Z' |
|---|---|---|---|---|---|
| 1 | 1 | 1 | 3 | $-CH_2-\overset{O}{\underset{\|}{C}}-CH_3$ | $-S-CH_2CH_2O-\overset{O}{\underset{\|}{C}}-CH_3$ |
| 1 | 1 | 1 | 3 | $-CH_2CH_2-\overset{O}{\underset{\|}{C}}-O-C_4H_9$ | $-S-CH_2-CH_2-O\overset{O}{\underset{\|}{C}}-C_7H_{15}$ |
| 1 | 1 | 1 | 3 | $-C_3H_6-\overset{O}{\underset{\|}{C}}-O-C_6H_{13}$ | $-S-C_3H_6O-\overset{O}{\underset{\|}{C}}-C_{17}H_{33}$ |
| 1 | 1 | 1 | 3 | $-C_2H_4-O-\overset{O}{\underset{\|}{C}}-C_3H_7$ | $-S-CH_2CH_2-O-\overset{O}{\underset{\|}{C}}-C_{11}H_{23}$ |
| 1 | 1 | 1 | 3 | $-C_3H_6-O-\overset{O}{\underset{\|}{C}}-C_{17}H_{35}$ | $-S-C_4H_8O-\overset{O}{\underset{\|}{C}}-C_5H_{11}$ |
| 1 | 1 | 1 | 3 | $-C_4H_8-O-\overset{O}{\underset{\|}{C}}-C_{11}H_{23}$ | $-S-CH_2CH_2-O-\overset{O}{\underset{\|}{C}}-C_{19}H_{39}$ |
| 1 | 1 | 1 | 3 | $-CH(\overset{O}{\underset{\|}{C}}-CH_3)_2$ | $-S-CH_2CH_2-O-\overset{O}{\underset{\|}{C}}-C_9H_{19}$ |
| 1 | 1 | 1 | 3 | $CH(\overset{O}{\underset{\|}{C}}-C_4H_9)_2$ | $-S-C_3H_6-O-\overset{O}{\underset{\|}{C}}-C_2H_5$ |
| 1 | 1 | 1 | 3 | $-CH(\overset{O}{\underset{\|}{C}}-C_{11}H_{23})_2$ | $-S-CH_2CH_2-O-\overset{O}{\underset{\|}{C}}-C_5H_{11}$ |
| 1 | 1 | 1 | 3 | $-CH(\overset{O}{\underset{\|}{C}}C_{17}H_{35})_2$ | $-S-CH_2CH_2-O-\overset{O}{\underset{\|}{C}}-C_{17}H_{35}$ |

-continued

| n | k | x | m | Y | Z' |
|---|---|---|---|---|---|
| 1 | 1 | 1 | 3 | $-C_2H_4-O-\overset{\overset{O}{\|}}{C}-H$ | $-S-CH_2CH_2-O-\overset{\overset{O}{\|}}{C}-C_{11}H_{23}$ |
| 1 | 1 | 1 | 3 | $-C_2H_4-\overset{\overset{O}{\|}}{C}-OH$ | $-S-C_3H_6-O-\overset{\overset{O}{\|}}{C}-C_{17}H_{35}$ |
| 1 | 1 | 1 | 3 | $-C_4H_8OH$ | $-S-CH_2CH_2-O-\overset{\overset{O}{\|}}{C}-C_5H_{11}$ |
| 1 | 1 | 1 | 5 | $-CH_2-\overset{\overset{O}{\|}}{C}-CH_3$ | $-S-CH_2CH_2-O-\overset{\overset{O}{\|}}{C}-C_7H_{15}$ |
| 1 | 1 | 2 | 8 | $-C_2H_4\overset{\overset{O}{\|}}{C}-O-C_6H_{13}$ | $-S-C_3H_6O-\overset{\overset{O}{\|}}{C}-C_{17}H_{35}$ |
| 1 | 1 | 1 | 5 | $-C_3H_6OH$ | $-S-C_4H_8O\overset{\overset{O}{\|}}{C}-C_{10}H_{19}$ |
| 1 | 1 | 1 | 3 | $-CH\left(-\overset{\overset{O}{\|}}{C}-O-CH_3\right)_2$ | $-S-CH_2CH_2-O-\overset{\overset{O}{\|}}{C}-C_7H_{15}$ |
| 1 | 1 | 1 | 3 | $-CH\left(-\overset{\overset{O}{\|}}{C}-C_8H_{17}\right)_2$ | $-S-C_3H_6-O-\overset{\overset{O}{\|}}{C}-C_{11}H_{23}$ |
| 1 | 1 | 1 | 3 | $-CH\left(-\overset{\overset{O}{\|}}{C}-C_{18}H_{37}\right)_2$ | $-S-C_4H_8-O-\overset{\overset{O}{\|}}{C}-C_{19}H_{39}$ |
| 1 | 1 | 1 | 3 | $-CH_2CH_2-\overset{\overset{O}{\|}}{C}-C_8H_{17}$ | $-S-CH_2CH_2-O\overset{\overset{O}{\|}}{C}-C_8H_{17}$ |
| 1 | 1 | 1 | 3 | $-C_4H_8-\overset{\overset{O}{\|}}{C}-C_{17}H_{35}$ | $-S-C_4H_8-O-\overset{\overset{O}{\|}}{C}-C_{11}H_{23}$ |

In accordance with this invention there are provided organotin mercaptoalkanol ester sulfide and polysulfide compounds according to the following formula.

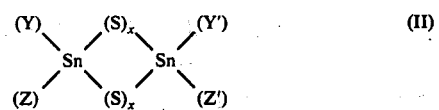

where Y, Y', Z, Z' and x are as previously defined herein. The polymer compositions, particularly the halogenated polymer compositions and more particularly vinyl halide homopolymer and copolymer compositions, according to this invention are compositions comprising an organic polymer and an organotin mercaptoalkanol ester sulfide or polysulfide according to the above formula. As examples of compounds according to formula (II) and of polymer compositions, particularly vinyl chloride homopolymer and copolymer compositions, of this invention containing compounds according to formula (II) there include, but not limited to, those compounds where

| x | y | y' | z | z' |
|---|---|---|---|---|
| 1 | $-CH_2-\overset{\overset{O}{\|}}{C}-CH_3$ | $-CH_2-\overset{\overset{O}{\|}}{C}-CH_3$ | $-S-CH_2CH_2-O\overset{\overset{O}{\|}}{C}-C_2H_5$ | $-S-CH_2CH_2-O-\overset{\overset{O}{\|}}{C}-C_2H_5$ |
| 1 | $-C_2H_4-\overset{\overset{O}{\|}}{C}-C_{12}H_{25}$ | $-CH_2-\overset{\overset{O}{\|}}{C}-CH_3$ | $-S-CH_2CH_2-O-\overset{\overset{O}{\|}}{C}-C_2H_5$ | $-S-CH_2CH_2-O-\overset{\overset{O}{\|}}{C}-C_2H_5$ |
| 1 | $-C_3H_6-O-C_2H_5$ | $-CH_2-\overset{\overset{O}{\|}}{C}-O-CH_3$ | $-S-CH_2CH_2-O-\overset{\overset{O}{\|}}{C}-C_5H_{11}$ | $-S-C_3H_6-O\overset{\overset{O}{\|}}{C}-C_{17}H_{35}$ |
| 2 | $-C_4H_8-O-C_{12}H_{25}$ | $-C_3H_6\overset{\overset{O}{\|}}{C}-O-C_{18}H_{37}$ | $-S-C_3H_6-O-\overset{\overset{O}{\|}}{C}-C_7H_{15}$ | $-C_2H_4OH$ |
| 1 | $-C_3H_6-OH$ | $-C_3H_6OH$ | $-S-C_3H_6-O-\overset{\overset{O}{\|}}{C}-C_{17}H_{35}$ | $-C_4H_9$ |
| 3 | $-C_2H_4\overset{\overset{O}{\|}}{C}-O-C_6H_{13}$ | $-C_3H_6-O-\overset{\overset{O}{\|}}{C}-C_{11}H_{23}$ | $-S-C_4H_8-O-\overset{\overset{O}{\|}}{C}-C_{11}H_{23}$ | $-CH_3$ |
| 2 | $-C_3H_6\overset{\overset{O}{\|}}{C}-OC_{18}H_{37}$ | $-CH_3$ | $-S-CH_2CH_2-O-\overset{\overset{O}{\|}}{C}-C_7H_{15}$ | $-CH_2-\overset{\overset{O}{\|}}{C}-CH_3$ |
| 1 | $-C_3H_6\overset{\overset{O}{\|}}{C}-OH$ | $-C_4H_9$ | $-S-C_3H_6-O-\overset{\overset{O}{\|}}{C}-C_{19}H_{39}$ | $-C_2H_4-O-C_6H_{13}$ |
| 2 | $-C_4H_8-O-\overset{\overset{O}{\|}}{C}-C_2H_5$ | $-C_{12}H_{25}$ | $-S-CH_2CH_2-O-\overset{\overset{O}{\|}}{C}-C_7H_{15}$ | $-C_3H_6O-\overset{\overset{O}{\|}}{C}-C_{17}H_{33}$ |
| 2 | $-C_2H_4-O-\overset{\overset{O}{\|}}{C}-C_{11}H_{23}$ | $-C_{18}H_{17}$ | $-S-CH_2CH_2-O-\overset{\overset{O}{\|}}{C}-C_{11}H_{23}$ | $-C_2H_4-\overset{\overset{O}{\|}}{C}-O-C_8H_{17}$ |

-continued

| x | y | y' | z | z' |
|---|---|---|---|---|
| 1 | —C₃H₆—O—C(=O)—C₁₇H₃₅ | Cl | —S—CH₂CH₂—O—C(=O)—C₁₇H₃₃ | —S—C₄H₈O—C(=O)—C₇H₁₅ |
| 3 | —CH—(O—C(=O)—CH₃)₂ | —C₂H₄C(=O)—O—C₈H₁₇ | —S—C₃H₆—O—C(=O)—C₇H₁₅ | Br |
| 4 | —CH(C(=O)—CH₃)₂ | —C₄H₈OH | —S—C₄H₈—O—C(=O)—C₆H₁₃ | I |
| 1 | —CH(C(=O)—C₅H₁₁)₂ | —CH(C(=O)—C₅H₁₁)₂ | —S—C₄H₈—O—C(=O)—C₈H₁₃ | —C₁₈H₃₇ |
| 1 | —CH(C(=O)—C₁₇H₃₅)₂ | —C₂H₄—O—CH₃ | —S—C₃H₆—O—C(=O)—C₉H₁₉ | —S—C₃H₆—O—C(=O)—C₉H₁₉ |

There are provided in accordance with this invention organotin mercaptoalkanol ester sulfide and polysulfide compounds of the following general formula

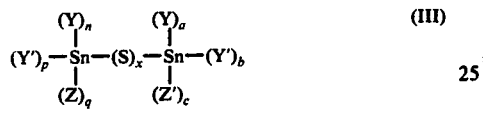

(III)

where Y, Y', Z, Z', a, b, c, n, p, q and x are as have been previously defined herein. Polymer compositions according to this invention are compositions comprising an organic polymer, more particularly a halogen containing organic polymer and an organotin mercaptoalkanol ester sulfide or polysulfide according to the above formula. Organotin mercaptoalkanol sulfides and polysulfides according to formula (III) and polymer, particularly vinyl halide homopolymer and copolymer, compositions according to the invention containing compounds according to formula (III) include but are not limited to compounds where

| a b c n p q x | Y | Y' | Z | Z' |
|---|---|---|---|---|
| 1 1 1 1 1 1 1 | —CH₂C(=O)—CH₃ | —CH₂—CH₃ | —S—CH₂CH₂OC(=O)—C₇H₁₅ | —S—CH₂CH₂OCC₇H₁₅ |
| 1 1 1 1 1 1 1 | —C₂H₄C(=O)CH₃ | —C₃H₆OCC₇H₁₅ | —S—C₃H₆OC(=O)—C₁₁H₂₃ | —S—CH₂CH₂OCC₁₇H₃₅ |
| 1 0 2 1 1 1 1 | —C₄H₈OCC₁₁H₂₃ | —C₂H₄C(=O)—OC₁₀H₂₁ | —S—C₄H₈OCC₁₇H₃₅ | —S—C₃H₆OCC₁₇H₃₅ |
| 0 2 1 1 0 2 1 | —C₃H₆COC₁₈H₃₇ | —C₃H₆C(=O)—OC₁₈H₃₇ | —S—C₃H₆OCC₂H₅ | —S—C₃H₆OCC₁₁H₂₃ |
| 1 1 1 1 1 1 1 | —C₂H₄C(=O)—OC₈H₁₇ | —CH₃ | —S—C₄H₈OCC₉H₁₉ | —CH₃ |
| 1 1 1 1 1 1 1 | —C₃H₆OCC₁₇H₃₅ | —C₄H₉ | —S—C₃H₆OCC₅H₁₁ | —C₈H₁₇ |
| 1 1 1 1 0 2 2 | —C₂H₄OCC₅H₁₁ | —C₄H₉OCC₂H₅ | —S—CH₂CH₂OCC₁₉H₃₉ | —C₄H₈OCC₂H₅ |
| 0 2 1 2 0 1 1 | —C₄H₈OCC₃H₇ | —C₂H₄O—C₃H₇ | —S—CH₂CH₂OCCH₃ | Cl |
| 2 0 1 1 1 1 3 | —C₃H₆OH | —C₂H₄OC₂H₅ | —S—C₃H₆OCC₃H₇ | —C₁₂H₂₅ |
| 2 0 1 1 0 2 2 | —C₂H₄C(=O)—OH | —C₂H₄—C(=O)—C₃H₇ | —S—C₄H₈OCC₁₄H₂₉ | —C₂H₄COC₈H₁₇ |
| 2 0 1 2 0 1 1 | —CH(CC₁₇H₃₅)₂ | | —S—C₃H₆OCC₁₅H₃₁ | —S—C₃H₆OCC₁₅H₃₁ |
| 1 1 1 2 0 1 2 | —C₂H₄—O—CH₃ | —C₄H₉ | —S—CH₂CH₂OCC₃H₇ | Br |
| 1 0 2 2 0 1 3 | —CH₂—O—C₈H₁₇ | | —S—C₄H₈OCC₇H₁₅ | —S—CH₂CH₂OCC₁₇H₃₃ |
| 1 0 2 1 0 2 1 | —C₃H₆—O—C₁₈H₃₇ | | —S—C₃H₆OCC₅H₁₁ | —C₄H₉ |
| 0 2 1 1 1 1 1 | —C₄H₈—O—C₁₂H₂₅ | —C₈H₁₆OH | —S—CH₂CH₂OCC₁₀H₂₁ | I |

-continued

| a b c n p q x | Y | Y' | Z | Z' |
|---|---|---|---|---|
| 0 1 2 2 0 1 2 | $-C_4H_8-\overset{O}{\underset{\|}{C}}-OC_{12}H_{25}$ | $-C_2H_4O\overset{O}{\underset{\|}{C}}-\text{C}_6\text{H}_5$ | $-S-CH_2CH_2O\overset{O}{\underset{\|}{C}}C_{17}H_{33}$ | $-S-C_3H_6O\overset{O}{\underset{\|}{C}}C_5H_{11}$ |
| 0 2 1 1 0 2 1 | $-C_3H_6-\overset{O}{\underset{\|}{C}}-O-C_6H_{13}-C_{18}H_{36}OH$ | | $-S-C_4H_8O\overset{O}{\underset{\|}{C}}CH_3$ | $-C_8H_{17}$ |
| 2 0 1 1 0 2 1 | $-CH_2\overset{O}{\underset{\|}{C}}-OC_2H_5$ | | $-S-CH_2CH_2O\overset{O}{\underset{\|}{C}}C_9H_{19}$ | $-S-CH_2CH_2O\overset{O}{\underset{\|}{C}}C_9H_{19}$ |
| 0 2 1 2 0 1 4 | $-C_4H_8-OH$ | $-C_{18}H_{37}$ | $-S-C_3H_6O\overset{O}{\underset{\|}{C}}C_8H_{17}$ | Cl |
| 0 2 1 2 0 1 1 | $-CH(\overset{O}{\underset{\|}{C}}-O-CH_3)_2$ | $-C_2H_4O\overset{O}{\underset{\|}{C}}C_5H_{11}$ | $-S-C_4H_8O\overset{O}{\underset{\|}{C}}C_4H_9$ | $-S-C_4H_8O\overset{O}{\underset{\|}{C}}C_4H_9$ |
| 0 1 2 2 0 1 1 | $-CH(\overset{O}{\underset{\|}{C}}-C_4H_9)_2$ | $-CH(\overset{O}{\underset{\|}{C}}-C_8H_{17})_2$ | $-S-CH_2CH_2O\overset{O}{\underset{\|}{C}}C_{15}H_{31}$ | $-S-CH_2CH_2O\overset{O}{\underset{\|}{C}}C_7H_{15}$ |
| 0 1 2 1 0 2 1 | $-CH(\overset{O}{\underset{\|}{C}}-C_8H_{17})_2$ | $-CH_2-\overset{O}{\underset{\|}{C}}-C_6H_{13}$ | $-S-CH_2CH_2O\overset{O}{\underset{\|}{C}}C_6H_{13}$ | $-S-C_3H_6O\overset{O}{\underset{\|}{C}}C_3H_7$ |
| 0 1 2 2 0 1 2 | $-CH(\overset{O}{\underset{\|}{C}}-C_{12}H_{25})_2$ | $-C_3H_6\overset{O}{\underset{\|}{C}}-OCH_3$ | $-S-C_3H_6O\overset{O}{\underset{\|}{C}}C_{19}H_{39}$ | $CH_3$ |
| 0 2 1 2 0 1 1 | $-CH(\overset{O}{\underset{\|}{C}}-C_{18}H_{37})_2$ | $-C_4H_9$ | $-S-C_4H_8O\overset{O}{\underset{\|}{C}}C_2H_5$ | $-S-C_3H_6O\overset{O}{\underset{\|}{C}}-CH_3$ |
| 1 1 1 2 0 1 1 | $-C_2H_4O-\overset{O}{\underset{\|}{C}}-C_7H_{15}$ | Cl | $-S-CH_2CH_2O\overset{O}{\underset{\|}{C}}C_7H_{15}$ | $-S-CH_2CH_2O\overset{O}{\underset{\|}{C}}C_7H_{15}$ |

The organotin mercaptoalkanol ester sulfides and polysulfides in accordance with this invention may be prepared by conventional techniques well-known in the art. In accordance with one such technique a mercaptoalkanol ester, sodium sulfide, ammonia and a mono-(oxoalkyl) tin trihalide are reacted together. A bis(oxoalkyl) tin dihalide or tris(oxoalkyl) tin halide may be appropriately substituted for the mono(oxoalkyl) tin trihalide. The term oxoalkyl is meant to identify alkyl ketones, esters and carboxylic acids which are bonded to the tin through a carbon atom of the alkyl group. In modifications of the above process there may be substituted for the oxoalkyltin halide an ester alkyltin halide wherein the ester alkyl group is bonded to the tin through a non carbonyl carbon atom of the esterifying carboxylic acid moiety or through a carbon atom of the esterifying alcohol moiety. Other organotin halide compounds, wherein the organo group or groups are bonded to tin through a non-carbonyl carbon atom of the organo group, which may be substituted for the oxoalkyltin halide in the above process include alkylether tin halides, hydroxy alkyltin halides and alkylcarboxylic acid tin halides. The preparation of oxoalkyltin halides is known in the art and particularly described in the Journal of The Chemical Society Chemical Communications Number 20/1976 pages 803 and 804, Kogyo Kagaku, Zasshi, 69(4) pages 649 to 653 and 1036 to 1039 (1966) and Chemical Abstracts 65, 18612 and 20160 (1968). The entire disclosures of which is incorporated herein by reference. The organotin halides usable in the above described art process can be replaced with corresponding organotin oxides or organostannoic acids for preparing the organotin mercaptoalkanol ester sulfides and polysulfides according to this invention. As the organotin halides usable in the art processes for preparing the organotin mercaptoalkanol ester sulfides and polysulfides of this invention there may be employed the organotin chlorides, bromides or iodides. Exemplary of the organotin chlorides there may be used, but not limited to acetylacetonyltin trichloride, bis(3-oxobutyl)tin dichloride, 3-oxobutyltin trichloride, 4-oxopentyltin trichloride, 3-carbobutoxypropyltin trichloride, carbo-isooctoxy-methyltin trichloride, bis(2-carbomethoxylethyl)tin dichloride and 2-carbomethoxylethyltin trichloride. Mercaptoalkanol esters as are described in Kugele et al U.S. Pat. No. 3,979,359 the entire disclosure of which is incorporated herein by reference, may be used in the above described art process for the preparation of the organotin mercaptoalkanol ester sulfides and polysulfides of this invention.

Organotin mercaptoalkanol ester sulfide and polysulfide compounds according to this invention are useful in stabilizing polymers. Particularly the compounds according to this invention, incorporated into organic polymers by methods and in amounts (e.g. 0.01 to 10%, usually 0.2 to 5%, by weight based on the polymer) well-known in the art, are useful in stabilizing halogen containing organic polymers (e.g. vinyl chloride homopolymers and copolymers).

As polymers, particularly halogen containing polymers, which can be used in the practice of the polymer compositions of this invention there include, but not limited to, in halogen-containing vinyl and vinylidene polymers, e.g., resins in which the halogen is attached directly to the carbon atoms. Preferably the polymer is a vinyl halide polymer, specifically a vinyl chloride polymer. Usually, the vinyl chloride polymer is made from monomers consisting of vinyl chloride alone or a mixture of monomers comprising at least 70% vinyl chloride by weight. When vinyl chloride copolymers are stabilized, preferably the copolymer of vinyl chloride with an ethylenically unsaturated compound copolymerizable therewith contains at least 10% of polymerized vinyl chloride.

As the chlorinated polymer there can be employed chlorinated polyethylene having 14 to 75%, e.g. 27% chloride by weight, chlorinated natural and synthetic rubber, rubber hydrochloride, chlorinated polystyrene, chlorinated polyvinyl chloride, polyvinyl chloride polyvinylidene chloride, polyvinyl bromide, polyvinyl fluoride, copolymers of vinyl chloride with 1 to 90%, preferably 1 to 30% of a copolymerizable ethylenically unsaturated material such as vinyl acetate, vinyl butyrate, vinyl benzoate, vinylidene, chloride, diethyl fumarate, diethyl maleate, other alkyl fumarates and maleates, vinyl propionate, methyl acrylate, 2-ethylhexyl acrylate, butyl acrylate and other alkyl acrylates, methyl methacrylate, ethyl methacrylate, butyl methacrylate and other alkyl methacrylates, methyl alpha chloroacrylate, styrene, trichloroethylene, vinyl ethers such as vinyl ethyl ether, vinyl chloroethyl ether and vinyl phenyl ether, vinyl ketones such as vinyl methyl ketone and vinyl phenyl ketone, 1-fluoro-2-chloroethylene, acrylonitrile, chloroacrylonitrile, allylidene diacetate and chloroallylidene diacetate. Typical copolymers include vinyl chloride-vinyl acetate (96:4 sold commercially as VYNW), vinyl chloride-vinylace-tate (87:13), vinyl chloride-vinyl acetate-maleic anhydride (86:13:1), vinyl-chloride-vinylidene chloride (95:5), vinyl chloride-diethyl fumarate (95:5), vinyl chloride-trichloroethylene (95:5), vinyl chloride-2-ethylhexyl acrylate (80:20). In addition to the novel compounds of this invention, there can also be incorporated with the resin, conventional additives such as plasticizers, pigments, fillers, dyes, ultraviolet light absorbing agents, densifying agents and the like. There can also be added conventional and known tin stabilizers e.g., those disclosed in Kauder et al U.S. Pat. No. 3,565,930 or Kugele et al 3,869,487 or in Weisfeld 3,640,950, Leistner 2,870,119 and 2,870,182, Best 2,731,484, Stefl 2,731,482 and Mack 2,914,506 for example. The entire disclosures of all the patents mentioned in this paragraph are hereby incorporated by reference.

If the plasticizer is employed, it is used in conventional amount, e.g. 10 to 150 parts per 100 parts of polymer. Typical plasticizers are di-2-ethylhexyl phthalate, dibutyl sebacate, dioctyl sebacate, tricresyl phosphate.

As indicated there can also be incorporated 0.1 to 10 parts per 100 parts of the halogen containing polymer of a metal salt stabilizer. Thus, there can be used barium, strontium, calcium, cadmium, zinc, lead, tin, magnesium, cobalt, nickel, titanium and aluminum salts of phenols, aromatic carboxylic acids, fatty acids or epoxy fatty acids.

Examples of suitable salts include barium di(nonylphenolate), strontium di(nonylphenolate), strontium di(amylphenolate), barium di(octylphenolate), strontium di(octylphenolate), barium di(nonyl-o-cresolate), lead di(octylphenolate), cadmium-2-ethyl hexoate, cadmium laurate, cadmium stearate, zinc caprylate, cadmium caprate, barium stearate, barium-2-ethylhexoate, barium laurate, barium ricinoleate, lead stearate, aluminum stearate, magnesium stearate, calcium octoate, calcium stearate, cadmium naphthenate, cadmium benzoate, cadmium p-tert, butylbenzoate, barium octyl salicylate, cadmium epoxy stearate, strontium epoxy stearate, cadmium salt of epoxidized acids of soybean oil, and lead epoxy stearate.

The organotin sulfides and polysulfides according to this invention in addition to being highly effective stabilizers are advantageously very low odor compounds, especially under polymer processing conditions. Additionally, the sulfides and polysulfides according to this invention advantageously should be of low toxicity.

In further describing this invention, embodiments thereof and the practice thereof the following non-limiting examples are offered. All percentages and amounts in the following examples are by weight unless otherwise indicated.

EXAMPLE 1

Into a 2 liter flask is placed 137 gms. (0.67 EQ.) of 2-mercaptoethylcaprylate, 450 ml of water, 130 gms. (0.34 EQ.) of 10% aq. sodium sulfide solution and 41 gms. (0.67 EQ.) of 28% of aq. ammonia. To the above, at 35° C. is added dropwise 108 gms. (1.0 EQ.) of acetylacetonyltin trichloride dissolved in 500 ml acetone, over a 30 minute period. The reactants are stirred under these conditions for one hour then the acetone removed under reduced pressure of 10 mm and 30° C. The remaining two layers are separated and the lower organic layer is washed with 250 ml of water. The product is then stripped to 100° C. under vacuum resulting in a 95% yield of yellow oil. Percent tin 17.6 (18.5), percent sulfur 13.0 (12.5), $n_D^{25}$ 1.5170 and Gardner color of 3. The product is mainly bis(acetylacetonytin di-2-mercaptoethylcaprylate) sulfide.

EXAMPLE 2

Into a 2 liter flask is placed 137 gms. (0.67 EQ.) of 2-mercaptoethylcaprylate, 450 ml water, 130 gms. (0.34 EQ.) 10% aq. sodium sulfide and 41 gms. (0.67 EQ.) of 28% aq. ammonia. To the above, at 35° C., is added dropwise, 79 gms. (0.5 EQ.) of bis(3-oxobutyl)tin dichloride and 50 gms. (0.5 EQ.) of 3-oxobutyltin trichloride dissolved in 500 ml acetone, over a 30 minute period. The reactants are stirred under these conditions for one hour then the acetone removed under reduced pressure at 30°-35° C. The remaining two layers are separated and the lower product layer washed with 200 ml of water. The product is then stripped to 100° C. under vacuum resulting in a 96% yield of yellow oil. Percent tin 21.9 (23.0), percent sulfur 11.9 (12.7), $n_D^{25}$ 1.5247; Gardner color 4. The product is a mixture of bis(3-oxobutyltin bis[2-mercaptoethylcaprylate])sulfide, bis(di-[3-oxobutyl]tin mono[2-mercaptoethylcaprylate])sulfide and (mono-3-oxobutyltin bis[2-mercaptoethylcaprylate]) di-[3-oxobutyl]tin mono[2-mercaptoethylcaprylate]sulfide.

EXAMPLE 3

Into a 2 liter flask is placed 230 gms. (0.67 EQ.) of 2-mercaptoethyloleate, 450 ml of water, 190 gms. (0.34 EQ.) of 10% aq. sodium disulfide and 41 gms. (0.67 EQ.) of 28% aq. ammonia. To the above, at 35° C., is added dropwise 103 gms. (1.0 EQ.) 4-oxopentyltin trichloride dissolved in 500 ml acetone, over a 30 minute period. The reactants are stirred under these conditions for one hour then the acetone removed under reduced pressure at 30°-35° C. The remaining two layers are separated and the lower product layer washed with 200 ml of water. The product is then stripped to 100° C. under vacuum resulting in a 93% yield of yellow oil. Percent tin 12.2 (12.9), percent sulfur 9.8 (10.5); $n_D^{25}$ 1.5133; Gardner color 3. The product is mainly bis[4-oxopentyltin bis(2-mercaptoethyloleate)]disulfide.

EXAMPLE 4

Into a 2 liter flask is placed 230 gms. (0.67 EQ.) of 2-mercaptoethyloleate, 500 ml benzene and 67.8 gms. (0.67 EQ.) of triethylamine. To the above at 30° C. is added portionwise 123 gms. (1.0 EQ.) of 3-carbobutoxypropyltin trichloride and allowed to stir for 30 minutes at this temperature. Then is added over a five minute period, at 25°–30° C., 130 gms. (0.34 EQ.) of 10% aqueous Na$_2$S and 500 ml of water. Stir for 10 minutes at 25° C. and separate layers. The upper product layer is washed with 300 ml of water and the product layer is stripped under reduced pressure slowly raising temperature to 100° C. The resultant product, a yellow oil, was obtained in 95% yield. Percent tin 11.3 (12.3), percent sulfur 9.2 (8.3); $n_D^{25}$ 1.5030; Gardner color 3. The product is bis[3-carbobutoxypropyltin-bis(2-mercaptoethyloleate)]sulfide.

EXAMPLE 5

Into a 2 liter flask is placed 69.5 gms. (0.34 EQ) of 2-mercaptoethylcaprylate, 500 gms. benzene and 34.5 gms. (0.34 EQ.) of triethylamine. To the above at 30° C. is added portion-wise 103 gms. (1.0 EQ.) of carbo-isoctoxymethyltin trichloride and allowed to stir for 30 minutes at this temperature. Then is added in one portion, at 25°–30° C., 260 gms. (0.67 EQ.) of sodium sulfide and 500 ml of water. Stir for 10 minutes and separate layers. The upper product layer is washed with 300 ml water and the product layer is stripped under reduced pressure slowly raising temperature to 100° C. The resultant product, a yellow oil, was obtained in 93% yield. Percent tin 21.7 (22.5), percent sulfur 11.9 (12.2); $n_D^{25}$ 1.5313; Gardner color of 2. The product is:

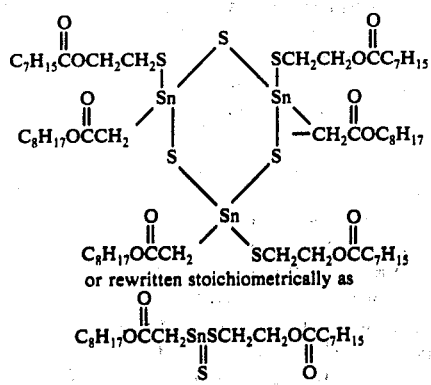

or rewritten stoichiometrically as $$C_8H_{17}OCCH_2SnSCH_2CH_2OCC_7H_{15}$$

EXAMPLE 6

Into a 2 liter flask is placed 201 gms. (0.58 EQ.) of 2-mercaptoethyloleate, 450 ml water, 130 gms. (0.34 EQ.) 10%. aq. sodium sulfide and 36 gms. (0.58 EQ.) of 28% aq. ammonia. To the above, at 35° C., is added dropwise 100 gms. (1.0 EQ.) of 3-oxobutyltin trichloride dissolved in 500 ml acetone. The reactants are stirred at 35° C. for one hour and then the acetone removed under reduced pressure at 30°–35° C. The remaining two layers are separated and the lower product layer washed with 200 ml of water. The product is then stripped to 100° C. under vacuum resulting in 93% yield of yellow oil. Percent tin 15.4 (16.0), percent sulfur 7.7 (8.7), $n_D^{25}$ 1.5194; Gardner color 4. The product is (mono-3-oxobutyltin bis[2-mercaptoethyloleate]) (mono-3-oxobutylmono chlorotin[2-mercaptoethyloleate])sulfide.

EXAMPLE 7

Into a three necked flask is placed 230 gms. (0.67 EQ.) of 2-mercaptoethyloleate, 450 ml of water, 190 gms. (0.34 EQ.) of 10% aq. sodium sulfide and 41 gms. (0.67 EQ.) of 28% aq. ammonia. To the above, at 25°–35° C., is added dropwise 104 gms. (1.0 EQ.) of 2-carbomethoxyethyltin trichloride, dissolved in 200 ml of toluene, over a ½ hour period. The reactants are stirred at room temperature for one hour, settled, lower water layer removed and the upper product layer stripped to 100° C. under vacuum, yielding 95% of a yellow liquid. Percent tin 13.4 (13.6), percent sulfur 8.5 (9.2); $n_D^{25}$ 1.5058, Gardner 4. The product is bis[2-carbomethoxyethyltin bis(2-mercaptoethyloleate)]sulfide.

EXAMPLE 8

Into a 2 liter flask is placed 173 gms. (0.50 EQ.) of 2-mercaptoethyloleate, 450 ml of water, 35 gms. (0.17 EQ.) isooctylthioglycolate, 130 gms. (0.34 EQ.) of 10% aq. sodium sulfide and 41 gms. (0.67 EQ.) of 28% aq. ammonia. To the above at 35° C. is added dropwise 100 gms. (1.0 EQ.) of 3-oxobutyltin trichloride in 500 ml acetone. The reactants are stirred at room temperature for one hour then the solvent removed under reduced pressure at 30°–35° C. The remaining 2 layers are separated and the lower product layer is washed with 200 ml of water. The product is then stripped to 100° C. under vacuum resulting in a 95% yield of pale yellow oil. Percent tin 14.7 (14.4); percent sulfur 9.2 (9.7)' $n_D^{25}$ 1.5098; Gardner 4. The product is mainly [(3-oxobutyltin bis[2-mercaptoethyloleate]) (3-oxobutyltinmono (2-mercaptoethyloleate) mono iso octylthioglycolate)]sulfide.

EXAMPLE 9

Into a 2 liter flask is placed 137 gms. (0.67 EQ.) of 2-mercaptoethylcaprylate, 450 ml of water, 130 gms. (0.34 EQ.) of 10% aq. sodium sulfide solution and 41 gms. (0.67 EQ.) of 28% aq. ammonia. To the above at 35° C., is added dropwise a mixture of 52 gms. (0.50 EQ.) of 2-carbomethoxyethyltintrichloride and 40 gms. (0.50 EQ.) of methyltintrichloride as a solution in 400 ml of toluene. The reactants are stirred at 25° C. for one hour, settled, lower water layer removed and the upper product layer stripped to 100° C. under vacuum, resulting in a 95% yield of a yellow oil. Percent tin 13.7 (13.8); percent sulfur 9.0 (9.3); $n_D^{25}$ 1.5070; Gardner 4. The product is mainly (mono 2-carbomethoxyethyltin bis[2-mercaptoethylcaprylate]) (monomethyltin(bis[2-mercaptoethylcaprylate])sulfide.

EXAMPLE 10

One hundred parts of polyvinyl chloride commercially available under the trade designation Geon 103 EP (B. F. Goodrich Chemical Co.) are admixed with 1.0 part OMYA 90T (fine particle size CaCO$_3$ coated with Ca stearate), 1.0 part TiO$_2$, 1.0 part of a paraffin wax commercially available under the trade designation ADVAWAX® 165 (Cincinnati Milacron Chemical Inc.), 0.1 part AC629A, Allied Chemical Corp., (oxidized low molecular weight ethylene homopolymer), 0.6 parts calcium stearate and stabilizer as as noted in Table I. The composition was placed on a mill having rolls with the front roll operating at 30 RPM and the rear roll at 40 RPM, heated to 380° F., and milled with sampling at one minute intervals after first introduction of mixture to the mill. The results of the test are found in Table I.

TABLE I

| Product Of Example No. | Tin Contained (mg.) | 1' | 2' | 3' | 4' | 5' | 6' | 7' | 8' | 9' | 10' |
|---|---|---|---|---|---|---|---|---|---|---|---|
| 1 | 40 | 9+ | 9 | 8 | 7 | 6 | 4+ | 4 | 2 | 2 | 1 |
| 2 | 40 | 10 | 10 | 9 | 7+ | 7 | 5+ | 4 | 3 | 2 | 1 |
| 3 | 40 | 10 | 9 | 8 | 7+ | 6 | 5 | 4 | 3 | 2 | 1 |
| 5 | 40 | 10 | 9 | 8 | 7 | 5+ | 4 | 4 | 3 | 2 | 1 |
| 7 | 40 | 10 | 10 | 9 | 8 | 7 | 6 | 4 | 4 | 3 | 2 |
| 10 | 40 | 10+ | 10 | 9+ | 9 | 8 | 7 | 6 | 5 | 5 | 3 |
| * | 40 | 9 | 8 | 7 | 6 | 5 | 4 | 4 | 3 | 2 | 1 |

COLOR SCALE: 10 (WHITE) 5 (TAN-ORANGE) 0 (BURN)

*This stabilizer consists of 25% monomethyltin tris(isooctylthioglycolate) and 75% dimethyltin bis(isooctylthioglycolate).

What is claimed is:

1. A composition comprising a halogen containing vinyl or vinylidene polymer and a stabilizingly effective amount of an organotin mercaptoalkanol ester sulfide or polysulfide having at least one sulfide or polysulfide bridged tin to tin group, at least one mercaptoalkanol ester group bonded to a sulfide or polysulfide bridged tin atom through the sulfur atom of the mercaptoalkanol moiety and at least one oxygen containing organic group bonded to a sulfide or polysulfide bridged tin atom through carbon said oxygen containing organic group being an organic group having a carbon oxygen bond, wherein the organotin mercaptoalkanol ester sulfide or polysulfide has the following formula

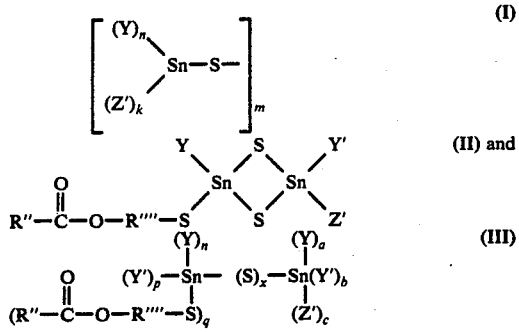

wherein $a$ is 0 to 2, $b$ is 0 to 2, $c$ is 1 or 2, $a+b+c$ is 3, $k$ is 1 or 2, $m$ is 3, $n$ is 1 or 2, $p$ is 0 or 1, $q$ is 1 or 2, $n+p+g$ is 3, $x$ is 1 or 2, $n+k$ is 2 or 3, Y is a member selected from the group consisting of

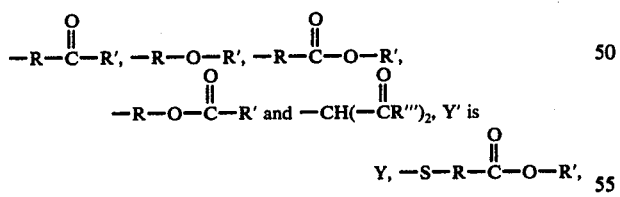

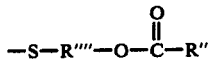

halogen of atomic weight 35 to 127, or alkyl of 1 to 18 carbon atoms, Z' is

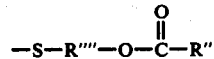

or Y', R is a bivalent hydrocarbon radical having 1 to 4 carbon atoms, R' is hydrogen or a monovalent hydrocarbon radical having 1 to 20 carbon atoms, R" is saturated or olefinically unsaturated alkyl of 1 to 20 carbon atoms, R''' is alkyl of 1 to 20 carbon atoms or alkoxy of 1 to 20 carbon atoms and R'''' is a bivalent hydrocarbon radical having two to four carbon atoms, with the proviso that in formula (I) at least one Z' is

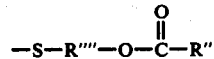

and the tin is tetravalent.

2. A composition according to claim 1 wherein the organic polymer is a vinyl halide homopolymer or copolymer.

3. A composition according to claim 1 wherein the organic polymer is a vinylidene halide homopolymer or copolymer.

4. A composition according to claim 1 wherein the organic polymer is homopolymer or copolymer of vinyl chloride.

5. A composition according to claim 4 wherein the organotin mercaptoalkanol ester sulfide or polysulfide is according to formula (I).

6. A composition according to claim 4 wherein the organotin mercaptoalkanol ester sulfide or polysulfide is according to formula (III).

7. A composition according to claim 1 wherein the organotin mercaptoalkanol ester sulfide or polysulfide is according to formula (I).

8. A composition according to claim 1 wherein the organotin mercaptoalkanol ester sulfide or polysulfide is according to formula (III).

9. A composition according to claim 7 wherein Y is -R-O-R'.

10. A composition according to claim 7 wherein Y is

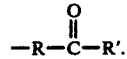

11. A composition according to claim 7 wherein Y is

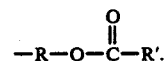

12. A composition according to claim 7 wherein Y is

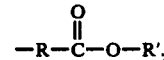

13. A composition according to claim 7 wherein Y is

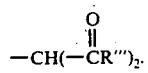

14. A composition according to claim 8 wherein Y is -R-O-R'.

15. A composition according to claim 8 wherein Y is

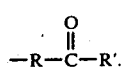

16. A composition according to claim 8 wherein Y is

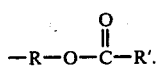

17. A composition according to claim 8 wherein Y is

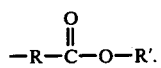

18. A composition according to claim 8 wherein Y is

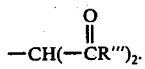

19. A composition according to claim 8 wherein X is 1.

20. A composition according to claim 8 wherein X is 2.

21. A composition according to claim 8 wherein $p$ is 0, $b$ is 0 and Z' is Z.

22. A composition according to claim 8 wherein Y' is alkyl of 1 to 18 carbon atoms.

23. An organotin mercaptoalkanol ester sulfide or polysulfide having the general formula

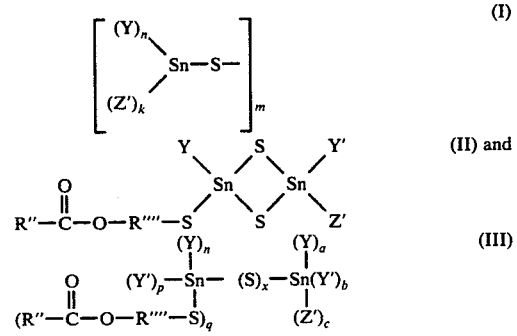

wherein $a$ is 0 to 2, $b$ is 0 to 2, $c$ is 1 or 2, $a+b+c$ is 3, $k$ is 1 or 2, $m$ is 3, $n$ is 1 or 2, $p$ is 0 or 1, $q$ is 1 or 2, $n+p+q$ is 3, $x$ is 1 or 2, $n+k$ is 2 or 3, Y is a member selected from the group consisting of

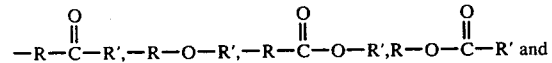

Y' is Y,

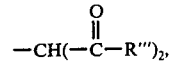

halogen of atomic weight 35 to 127 or alkyl of 1 to 18 carbon atoms, Z' is

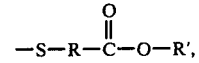

or Y', R is a bivalent hydrocarbon radical having 1 to 4 carbon atoms, R' is hydrogen or a monovalent hydrocarbon radical having 1 to 20 carbon atoms, R" is saturated or olefinically unsaturated alkyl of 1 to 20 carbon atoms, R''' is alkyl of 1 to 20 carbon atoms or alkoxy of 1 to 20 carbon atoms and R'''' is a bivalent hydrocarbon radical having two to four carbon atoms, with the proviso that in formula (I) at least one Z' is

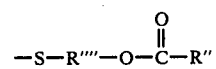

and the tin is tetravalent, said organotin mercaptoalkanol ester sulfide and polysulfide having at least one sulfide or polysulfide bridged tin to tin group, at least one mercaptoalkanol ester group bonded to sulfide or polysulfide bridged tin atom through the sulfur atom of the mercaptoalkanol moiety and at least one oxygen containing organic group bonded to a sulfide or polysulfide bridged tin atom through carbon said oxygen containing organic group being an organic group having a carbon oxygen bond.

24. An organotin mercaptoalkanol ester sulfide or polysulfide according to claim 23 having formula (I) of claim 23.

25. An organotin mercaptoalkanol ester sulfide or polysulfide according to claim 23, having formula (II) of claim 23.

26. An organotin mercaptoalkanol ester sulfide or polysulfide according to claim 23 having formula (III) of claim 23.

27. An organotin mercaptoalkanol ester sulfide or polysulfide according to claim 24 wherein Y is

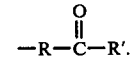

28. An organotin mercaptoalkanol ester sulfide or polysulfide according to claim 24 wherein Y is

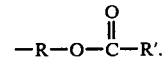

29. An organotin mercaptoalkanol ester sulfide or polysulfide according to claim 24 wherein Y is

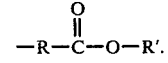

30. An organotin mercaptoalkanol ester sulfide or polysulfide according to claim 24 wherein Y is

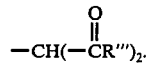

31. An organotin mercaptoalkanol ester sulfide or polysulfide according to claim 24 wherein Y is —R-O-R'.

32. An organotin mercaptoalkanol ester sulfide or polysulfide according to claim 26 wherein Y is

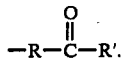

33. An organotin mercaptoalkanol ester sulfide or polysulfide according to claim 26 wherein Y is -R-O-R'.

34. An organotin mercaptoalkanol ester sulfide or polysulfide according to claim 26 wherein Y is

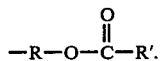

35. An organotin mercaptoalkanol ester sulfide or polysulfide according to claim 26 wherein Y is

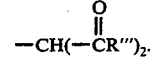

36. An organotin mercaptoalkanol ester sulfide or polysulfide according to claim 26 wherein Y is $$-CH(-\overset{O}{\underset{\|}{C}}R''')_2.$$

37. An organotin mercaptoalkanol ester sulfide or polysulfide according to claim 29 wherein Y is

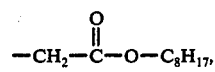

$k$ is 1, $n$ is 1, and $m$ is 3.

38. An organotin mercaptoalkanol ester sulfide or polysulfide according to claim 26 wherein $x$ is 1.

39. An organotin mercaptoalkanol ester sulfide polysulfide according to claim 26 wherein $x$ is 2.

40. An organotin mercaptoalkanol ester sulfide or polysulfide according to claim 26 wherein $p$ is 0, $b$ is 0 and Z' is Z.

41. An organotin mercaptoalkanol ester sulfide or polysulfide according to claim 26 wherein $b$ is 1 and Y' is chlorine.

42. An organotin mercaptoalkanol ester sulfide or polysulfide according to claim 26 wherein Y' is alkyl of 1 to 18 carbon atoms.

43. A composition according to claim 1 wherein the organotin mercaptoalkanol ester sulfide or polysulfide is according to formula (II).

* * * * *